United States Patent [19]
Schreier et al.

[11] Patent Number: 6,150,552
[45] Date of Patent: Nov. 21, 2000

[54] EFFICIENT METHODS FOR MAKING TETRAHALOPHTHALATE ESTERS HAVING EXCELLENT PURITY

[75] Inventors: Jeffrey A. Schreier; James D. Siebecker, both of West Lafayette; Arthur G. Mack, Lafayette, all of Ind.

[73] Assignee: Great Lakes Chemical Corporation, West Lafayette, Ind.

[21] Appl. No.: 09/343,316

[22] Filed: Jun. 30, 1999

Related U.S. Application Data

[60] Provisional application No. 60/091,398, Jun. 30, 1998.

[51] Int. Cl.[7] .............................. C07C 69/76; C08K 5/09
[52] U.S. Cl. ................................................................ 560/78
[58] Field of Search ........................ 560/78, 79; 562/485

[56] References Cited

U.S. PATENT DOCUMENTS

| | | | |
|---|---|---|---|
| 4,284,793 | 8/1981 | Sagara | 560/78 |
| 4,298,517 | 11/1981 | Sandler | 260/31.8 |
| 4,304,925 | 12/1981 | Watanabe et al. | 560/78 |
| 4,376,837 | 3/1983 | Jenkner et al. | 524/108 |
| 4,754,053 | 6/1988 | Mamuzic et al. | 560/78 |
| 4,912,158 | 3/1990 | Bohen et al. | 524/288 |
| 5,208,366 | 5/1993 | Bohen et al. | 560/83 |
| 5,728,323 | 3/1998 | Day et al. | 252/601 |

FOREIGN PATENT DOCUMENTS

WO 98/57920  12/1998  WIPO.

*Primary Examiner*—Gary Geist
*Assistant Examiner*—Sherif A. Kafafi
*Attorney, Agent, or Firm*—Woodard, Emhardt, Naughton, Moriarty & McNett

[57] ABSTRACT

Provided are methods for the preparation and purification of alkyl tetrahalophthalate esters by the reaction of a tetrahalophthalic compound with an alkanol in the presence of a titanate catalyst. More particularly, improved methods are provided for making and recovering an ester with little contamination by catalytic metal components and color bodies, and with little acidity, in a high yield from the esterification reaction by pretreating the starting materials to reduce the acidity thereof, reacting the starting materials in the presence of a titanate catalyst, stripping excess alcohol, hydrolyzing the catalyst, and filtering out solids to yield a high purity tetrahalophthalate ester product.

38 Claims, No Drawings

EFFICIENT METHODS FOR MAKING TETRAHALOPHTHALATE ESTERS HAVING EXCELLENT PURITY

This application claims the benefit of U.S. Provisional No. 60/091,398 filed Jun. 30, 1998.

BACKGROUND OF THE INVENTION

1. Field of the Invention

The invention relates to the preparation and purification of alkyl tetrahalophthalate esters, the esters being produced by the reaction of a tetrahalophthalic compound with an alkanol in the presence of a titanate catalyst. More particularly, it relates to improved methods for making and recovering an ester with little contamination by catalytic metal components and color bodies, and with little acidity, in a high yield, from the esterification reaction.

2. Discussion of Related Art

Processes are known in the prior art for making tetrahalophthalate esters by reacting a tetrahalophthalic acid or its anhydride with an organic alcohol in the presence of a catalyst. A wide variety of catalysts may be used for such a reaction. A class of catalysts that experienced a good deal of popularity in the past for this type of reaction is acid catalysts. While the use of acidic catalysts such as sulfuric acid, phosphoric acid, toluene sulfonic acid and methanesulfonic acid to prepare halogenated esters of phthalic acid is known, the use of this type of catalyst typically results in poor yield and poor product quality, particularly with respect to color and residual acidity. Reaction rates are also typically very slow.

It has become increasingly common, especially in the esterification of aromatic carboxylic acids and their anhydrides, to utilize an organometallic compound as an esterification catalyst. It is known, for example, that titanate catalysts (also referred to as alkyl titanate catalysts, tetraalkyl titanate catalysts or titanium alkoxides), including compounds such as tetraisopropyl titanate, tetra-n-butyl titanate, tetra-2-ethylhexyl titanate or the polymers thereof, are useful as catalysts in such a reaction.

These catalysts, and others, have been widely used commercially and are generally accepted as being among the best catalysts for esterification reactions. Recent efforts to improve efficiency and product quality in processes for making and recovering tetrahalophthalate esters, have therefore focused upon reactions utilizing a titanate catalyst. Even esterification reactions using tetraalkyl titanates as catalysts, however, problematically yield a product that, while improved over those prepared with acid catalysts, still does not have the quality for applications requiring extremely low acidity, color, residual ionics, and metallic catalyst residues. A major problem that has heretofore prevented successful preparation of high purity tetrahalophthalate ester products, for example, is that the titanate catalyst is difficult to remove from the crude reaction product without causing adverse consequences. A further undesirable result, especially in the production of tetrahalophthalate esters, is significant residual acidity in the reaction product.

Tetrahalophthalate esters prepared by known routes, therefore, are often contaminated with unacceptable levels of residual metal ions, acidity, solvent, and have higher color than their unhalogenated counterparts. Because tetrahalophthalate esters are widely used as plasticizers in polyvinylchloride ("PVC") used as insulation in wire and cable, such contamination and acidity is a significant problem. The presence of residual metals ions, for example, is of increasing importance because of their effects on electrical properties of such wire and cable insulation products. The presence of solvent in the ester product can cause bubbling and flashing when compounded in PVC, and also causes the product to have a strong odor as the product emits alcohol fumes. Color contamination is problematic, for example, because the product is commonly used in colored products and the presence of color bodies in the ester can discolor a final product, especially a light color final product.

A number of methods have been proposed to achieve removal of titanate catalysts from the reaction product; however, methods for removing the catalyst have commonly been found to have adverse effects on other product features, such as, for example, acidity, yield, filterability and product quality. For example, U.S. Pat. No. 4,284,793 to Sagara, which, along with all other patents cited herein, is incorporated by reference herein in its entirety, describes a method for producing a plasticizer with low residual titanium. In the method described in Sagara, phthalic anhydride is reacted with an alcohol in the presence of a titanate catalyst and then a solid alkali and an adsorbing agent are added to the reaction mixture in the absence of water. Subsequently, the product is filtered. This methodology, however, is not described as being useful to make halogenated phthalate esters, and treatment of a tetrabromophthalate ester crude reaction product in this way has been reported to result in an unfilterable product.

U.S. Pat. No. 4,304,925 to Watanabe describes a method for removing organometallic residues from a crude organic ester reaction product by treating the crude product with water and then treating the product with a base such as sodium carbonate or sodium hydroxide. This patent, however, also does not describe methods for making halogenated phthalate esters, and it has been reported that when a tetrabromophthalate ester is produced by this method, the product is unfilterable and esterification rates are very slow.

Mamuzic et al. (U.S. Pat. No. 4,754,053) describes purification of tetrabromophthalate esters by treatment of the crude reaction product with sodium carbonate decahydrate followed by filtration. This process has not been found to produce the ester product without the aforementioned impurities. Additionally, with the method described in Mamuzic, the filtered product develops haze over time. U.S. Pat. No. 5,728,323 to Day discloses a method in which a tetrahalophthalic anhydride or acid is dissolved in an excess amount of one or more alkanols having an alkyl group of $C_1$–$C_{18}$. Residual sulfuric acid is removed by treatment with aqueous magnesium acetate or multiple water washes. Esterification with a tetraalkyl titanate catalyst is followed by removal of residual acidic components by treatment with a Group II alkali metal salt, such as magnesium silicate. It has been found, however, that this process also fails to produce a product having a desirable purity, and this process is also extremely uneconomical, requiring expensive drying steps due to the addition of water to the starting materials, and also requiring the use of expensive Group II alkali metal salts.

Methods in the prior art, therefore, continue to suffer from the problems of inefficiency, acidity and the presence of metal ions and color bodies. It has also been reported that many prior art methods produce ester products with high levels of residual sodium ions, which results in significant end-use disadvantage, and feature filtration rates that are very slow, leading to low productivity and high manufacturing costs.

In view of the above background, the present invention satisfies a long-felt need in the prior art by providing efficient and economical methods for the preparation of high purity tetrahalophthalate esters. Using inventive methods, impurities and acidity in the ester product are minimal and yield and productivity are excellent.

SUMMARY OF THE INVENTION

The present invention provides methods for the preparation and purification of alkyl tetrahalophthalate esters made by the reaction of a tetrahalophthalic compound with an alkanol in the presence of a titanate catalyst. More particularly, improved methods are provided for making and recovering an ester with little contamination by impurities, such as catalytic metal components and color bodies, and with little acidity, in a high yield from the esterification reaction. The invention involves pretreating the tetrahalophthalic compound used as a starting material to reduce the acidity thereof, reacting the starting materials in the presence of a titanate catalyst, stripping excess alcohol, hydrolyzing the catalyst, and filtering out solids to yield a high purity tetrahalophthalate ester product.

In a preferred aspect of the present invention, there is provided a method for making a tetrahalophthalate ester featuring reduced levels of metal ion contamination, color body contamination and acidity, comprising (1) providing a pretreated mixture including a tetrahalophthalic compound, a first organic alcohol, sulfuric acid and a member selected from the group consisting of sodium carbonate, sodium bicarbonate, potassium carbonate, potassium bicarbonate or a combination thereof; wherein the sulfuric acid:tetrahalophthalic compound ratio is less than about 4:10,000 by weight; (2) subjecting the pretreated mixture to reflux conditions in the presence of a titanate catalyst for a period of time effective to yield a crude reaction product, the crude reaction product including a tetrahalophthalate ester, a portion of the first organic alcohol that remained unreacted and the titanate catalyst; (3) removing a substantial portion of the first organic alcohol from the crude reaction product to provide a stripped product; (4) hydrolyzing the titanate catalyst in the stripped product by introducing an aqueous base selected from the group consisting of sodium carbonate, sodium bicarbonate, potassium carbonate, potassium bicarbonate and a combination thereof into the stripped product to provide an aqueous intermediate; (5) removing water from the aqueous intermediate to provide a nonaqueous intermediate; (6) dispersing a solid adsorbent into the nonaqueous intermediate to provide a slurry; and (7) filtering the slurry to produce a filter cake and a tetrahalophthalate ester product. It is preferred that the pretreated mixture be essentially free from water.

In one preferred aspect of the invention, the mixture is provided by first providing a mixture including the organic alcohol and tetrahalophthalic compound, wherein the mixture also includes sulfuric acid in a sulfuric acid:tetrahalophthalic compound ratio of at least about 4:10,000 by weight, and then pretreating the mixture to reduce the acidity of the mixture and provide a pretreated mixture having a sulfuric acid:tetrahalophthalic compound ratio of less than about 4:10,000 by weight. The pretreating preferably comprises introducing into the mixture sodium carbonate, sodium bicarbonate, potassium carbonate, potassium bicarbonate or a combination thereof (a "neutralizing base") in an amount effective to reduce the acidity. The carbonates are the most preferred compounds, and, in particular, sodium carbonate is preferred. It is preferred that the neutralizing base be substantially dry. The amount of sodium carbonate introduced into the mixture is preferably determined by the following equation:

$$gNa_2CO_3 = \frac{g\,PHT\text{-}4 \times (\%H_2SO_4 - N)}{1} \times \frac{106.1}{100 \times 98.08}$$

wherein "g PHT-4" is the mass in grams of the tetrabromophthalic anhydride; wherein "%$H_2SO_4$" is the weight percent of $H_2SO_4$ as compared to the mass of the tetrabromophthalic compound; wherein "N" is the desired weight percent of $H_2SO_4$ in the pretreated mixture and is from about 0.01 to about 0.04; and wherein "g$Na_2CO_3$" is the mass in grams of sodium carbonate that is introduced into the mixture.

In another preferred aspect of the invention, the mixture is provided by first pretreating a composition including a tetrahalophthalic compound contaminated with sulfuric acid, to provide a pretreated composition having a sulfuric acid:tetrahalophthalic compound ratio of less than about 4:10,000 by weight. The composition is preferably pretreated by introducing into the composition sodium carbonate, sodium bicarbonate, potassium carbonate, potassium bicarbonate or a combination thereof in an amount effective to reduce the acidity. The pretreated composition is then mixed with an organic alcohol with the to provide a pretreated mixture.

As an alternative to the above, the pretreated composition may advantageously be provided by simply introducing the starting materials into a container in proportions selected in accordance with the invention and stirring the same to achieve neutralization of residual sulfuric acid.

In a preferred aspect of the invention, the filtering of the slurry is accomplished by passing the slurry through a bed of diatomaceous earth. Because the filter cake produced by this filtering has been found to include a portion of unrecovered tetrahalophthalate ester, another aspect of the invention includes dispersing the filter cake in a solvent to provide a second slurry, and filtering the second slurry to provide a recovery composition comprising the solvent and a recovered tetrahalophthalate ester product. The solvent is preferably an organic alcohol, and may more preferably comprise an organic alcohol that is substantially the same composition as the organic alcohol used in the initial esterification reaction.

In one preferred aspect of the invention, the tetrabromophthalate ester in the recovery composition is recycled by combining the recovery composition with a second quantity of a tetrahalophthalic compound and reacting the tetrahalophthalic compound with the second organic alcohol to produce a second tetrahalophthalate ester product. Alternatively, the solvent may simply be removed from the recovery composition to provide a third tetrabromophthalate ester product.

It is an object of the present invention to provide methods for producing low color, high purity dialkyl tetrahalophthalate esters, which may be used as plasticizers and fire retardants, with low acid values. Products known in the art do not have such a low acidity and such a low concentration of sodium, residual metals, and other color-causing components as products prepared in accordance with the invention.

Further objects, advantages and features of the present invention will be apparent from the detailed description herein.

DESCRIPTION OF THE PREFERRED EMBODIMENTS

For purposes of promoting an understanding of the principles of the invention, reference will now be made to particular embodiments of the invention and specific language will be used to describe the same. It will nevertheless be understood that no limitation of the scope of the invention is thereby intended, such alterations and further modifications in the invention, and such further applications of the principles of the invention as described herein being contemplated as would normally occur to one skilled in the art to which the invention pertains.

This invention serves to provide improved methods for the preparation of dialkyl tetrahalophthalate esters, in which the ester product features low acidity, low color, low haze and low residual metal ions, and in which the ester product is obtained consistently with retention of good filterability. Filtration rates are important if an economical process is to be achieved.

In a preferred aspect of the invention, a tetrahalophthalic compound, preferably tetrahalophthalic anhydride or tetrahalophthalic acid, is dissolved in an excess of alcohol solvent and residual sulfuric acid therein is partially neutralized by the addition of sodium carbonate. After neutralization, an alkyl titanate catalyst is added and the mixture is heated to reflux until the reaction is complete, thereby producing a crude reaction product. After removing the solvent, preferably by distillation, the catalyst is hydrolyzed by contact with an aqueous base selected in accordance with the invention, water is removed, preferably by distillation, and an adsorbent, such as, for example, activated carbon, magnesium silicate and/or diatomaceous earth (i.e., celatom), or combinations thereof, is added to the stirred mass. The resulting slurry is then filtered to produce a product with an excellent combination of color, clarity, acidity and ionics not achieved in the prior art. The filter cake may then advantageously be re-slurried with solvent and filtered to recover product that would otherwise be lost to the filter cake. The filtrate can either be stripped to leave pure product or, if the same solvent is used as in the reaction step, can be recycled to the next reaction.

The tetrahalophthalic compound used in accordance with the invention may be of tetrabromo- or tetrachloro-substitution on the aromatic ring. A tetrabromophthalic compound is preferred, and tetrabromophthalic ahnydride is the most preferred tetrahalophthalic compound. While the present specification makes reference primarily to tetrabromophthalic anhydride, it is understood that the principles of the invention apply as well to alternative tetrahalophthalic compounds.

Typically, a tetrahalophthalic compound is made in a process utilizing oleum and the elemental halide, resulting in a product which has substantial amounts of residual sulfuric acid. Residual acidity in the tetrahalophthalic compound used in the production of tetrahalophthalate esters results in poor ester product purity and poor color. Neutralization is therefore an important consideration in inventive methods.

The alcohol used in inventive methods is preferably a primary or secondary alkanol with linear or branched alkyl moieties having from about 1 to about 18 carbon atoms, more preferably from about 4 to about 16 carbon atoms. For example, excellent alcohols include 2-ethylhexanol, n-butanol, isobutanol, heptanol, nonanol, decanol, decyl alcohol and the like, and mixtures thereof. The alcohol may also be a mixture of alkanols resultant from Oxo and Ziegler manufacturing processes as known in the art (see Weissermei, K. and Arpe, H-J., *Industrial Organic Chemistry,* pages 132–134, 206–208, VCH Publishers, New York, 1978). A preferred alcohol used in accordance with the invention is 2-ethylhexanol.

Because residual sulfuric acid is typically present in tetrabromophthalic anhydride from its manufacture, either the tetrabromophthalic anhydride starting material, or a mixture of the same with other starting materials, is pretreated to neutralize at least a portion of the sulfuric acid present therein. Residual sulfuric acid in the mixture is preferably at least partially neutralized by adding to the anhydride or the mixture a base selected from the group consisting of sodium carbonate, sodium bicarbonate, potassium carbonate, potassium bicarbonate or a combination thereof. In a preferred embodiment of the invention, sodium carbonate is used to neutralize the sulfuric acid. The remaining or un-neutralized sulfuric acid is preferably less than about 0.04 wt %, and more preferably from about 0.01 to about 0.04 wt % of the original charge of tetrabromophthalic anhydride.

It is important that the amount of base introduced into the mixture be carefully controlled to prevent under-neutralization or over-neutralization of the sulfuric acid. Over-neutralization results in the undesirable production of alkyl tetrabromobenzoates in the final product. Alkyl tetrabromobenzoates result from the decarboxylation of the mono alkyl tetrabromo ester (half ester). Under-neutralization (i.e., higher residual acidity) leads to a higher colored product as more colored bodies are formed in the reaction step. Other unwanted side reactions also occur such as ether formation caused by the residual acid.

When using sodium carbonate to pretreat the anhydride or the mixture, it is preferred that the amount of sodium carbonate added be determined in accordance with the following equation:

$$g Na_2CO_3 = \frac{g\, PHT\text{-}4 \times (\% H_2SO_4 - N)}{1} \times \frac{106.1}{100 \times 98.08}$$

wherein "g PHT-4" is the mass in grams of the tetrabromophthalic compound; wherein "$\% H_2SO_4$" is the weight percent of $H_2SO_4$ as compared to the mass of the tetrabromophthalic compound; wherein "N" is the desired weight percent of $H_2SO_4$ in the pretreated anhydride or mixture (typically from about 0.01 to about 0.04) and wherein "$gNa_2CO_3$" is the calculated mass in grams of sodium carbonate that is to be introduced into the anhydride or mixture. By using this equation, the appropriate amount of sodium carbonate will be added, thereby preventing the over-neutralization or under-neutralization of the mixture. It is readily understood that a similar equation, modified to account for the different molecular weights and neutralizing functionality, may be used to calculate the appropriate amount of sodium bicarbonate, potassium carbonate or potassium bicarbonate to be added. Such modification can be readily made by a person of ordinary skill in the art without undue experimentation.

The neutralizing base may be introduced in the form of an aqueous solution; however, when an aqueous base is introduced, the water must be removed prior to the esterification reaction. It is therefore preferred that the base be substantially dry when mixed with the anhydride or the mixture. It is preferred that the base be introduced in the form of a particulate solid.

The pretreated mixture is then heated to reflux in the presence of a catalyst, preferably with removal of water from the reflux environment, to provide a crude reaction product. Reflux temperature range is preferably from about 180° C. to about 260° C. Temperatures between about 190° C. and about 220° C. are more preferred. Reaction times preferably range between about 3 and about 24 hours. Reactions may be considered complete when the acid value is less than about 1 meq/100 g when titrated against bromothymol blue. Reactions ending with higher acid values result in a green tinted product or products that contain acidity and ionics.

As stated above, a titanium catalyst is preferably used to achieve esterification of the tetrahalophthalic compound. It is preferred that inventive processes utilize alkyl titanates (also referred to as titanium alkoxides or tetraalkyl titanates) to catalyze these reactions. Alkyl titanates have been found to yield products with excellent color in relatively short reaction times. Furthermore, the alkyl titanate is readily rendered insoluble in a stripped reaction product in accordance with the invention by hydrolysis, rendering the catalyst more readily removable.

The catalyst may advantageously be a titanium $C_{2-4}$ alkoxide such as the ethoxide, propoxides and butoxides of titanium (IV). Titanium isopropoxide is especially preferred. Further, the titanate catalyst may be selected whereby the alkyl moiety therein corresponds to that of the alcohol being used to react with the tetrahalophthalic compound to produce an ester according to the invention. For example, in a method in which 2-ethylhexanol is used in the esterification reaction, an excellent catalyst that may advantageously be used is 2-ethylhexyl titanate. Similarly, in a method in which octanol is used in the esterification reaction, an excellent catalyst that may be used is octyl titanate. As such, examples of catalysts that may be used include 2-ethylhexyl titanate, octyl titanate, isopropyl titanate, butyl titanate and mixtures thereof. It is understood that the above list is not intended to limit the invention, but simply to provide examples of catalysts that may be advantageously used in accordance with the invention. A wide variety of titanate catalysts, including those mentioned above, are readily available commercially.

After the esterification reaction is complete, the remaining (unreacted) alcohol is removed from the crude reaction product, preferably by vacuum distillation, to yield a stripped product. An important feature of this invention is that hydrolysis of the titanate catalyst is performed after removal of the alcohol. Hydrolysis prior to alcohol removal results in solids that cause fouling in the distillation equipment. To achieve hydrolysis in accordance with the invention, water and sodium carbonate may preferably be added to the stripped product at a temperature of about 20–115° C., thereby providing an aqueous intermediate. The amount of water added in this aspect of the invention is preferably about 0.1 to 5% of the weight of product, and the amount of sodium carbonate added is preferably about 0.1 to 5%. The most preferred amount for both is about 1%. Although hydrolysis is not necessary to remove the titanate, it greatly increases filtration rates when removing activated carbon as well as preventing activated carbon breakthrough resulting in a hazy product. As an alternative to sodium carbonate, compositions that may be added to achieve hydrolysis in accordance with the invention include sodium bicarbonate, potassium carbonate, potassium bicarbonate or a combination thereof. It is understood that the amounts of these composition that would preferably be added may be adjusted by a person of ordinary skill in the art to account for the differing molecular weights and functionalities thereof. The water is then removed from the aqueous intermediate, preferably by vacuum distillation, to provide a nonaqueous intermediate. Removing the water in this way also advantageously results in lower alcohol content of the final product.

A solid adsorbent, preferably activated carbon, is then added to the nonaqueous intermediate with stirring to provide a slurry. While it is not intended that the invention be limited by any theory whereby it achieves its advantageous result, it is believed that activated carbon serves a variety of advantageous functions in the slurry. For example, it is believed that activated carbon not only removes color bodies resulting in a low colored product, but also greatly reduces metals ions and acidity of the final product. Color is an important characteristic of flame-retardant plasticizers, such as the tetrahalophthalate esters made in accordance with the invention, when they are used in clear or dyed polymers systems. Removal of metal ions and salts by the activated carbon is important as the resulting product has better electrical properties when incorporated into a polymer used in wire and cable applications. Activated carbon is also believed to aid in the lowering of acidity. The half ester is acidic unless deprotanated and containing a counter ion. The monoester increases acidity, and the metal counter ions lower electrical properties. The process of activated carbon treatment and filtration also improves the clarity of the flame retardant, and carbon treated product also shows much improved heat stability. When the carbon treated product is heated to about 150° C., acidity rises slowly, with untreated material the acidity rises rapidly and haze develops leaving a cloudy product. Heat stability is important for subsequent processing of the product in polymer systems.

In addition to activated carbon, magnesium silicate and/or diatomaceous earth can be added to the nonaqueous intermediate. It is believed that magnesium silicate also assists in lowering the acidity and color of the final product. It is also believed that diatomaceous earth helps to prevent blinding and to increase filtration rates during removal of solids.

After the solid adsorbent is added, the slurry is preferably stirred at a temperature of from about 60° C. to about 150° C., with a range of about 90° C. to about 115° C. being more preferred. The slurry is preferably stirred for about 1 to about 24 hours, more preferably from about 1 to about 12 hours, and most preferably from about 1 to about 6 hours. Solids are then removed by filtration, preferably through a bed of diatomaceous earth to provide a purified ester product.

Filter cake produced by this invention typically contains from about 30% to about 70% dialkyl tetrahalophthalate. This would typically correlate to a loss of from about 5% to about 20% of the ester product to the filter cake. In an additional aspect of the invention, therefore, the economical value of the process is enhanced by recovering product lost to the filter cake. In this regard, spent activated carbon cake may advantageously be slurried in a solvent and re-filtered to provide a filtrate recovery composition including a substantial portion of the solvent and the tetrabromophthalate ester product that was left in the filter cake.

The recovery composition can be recycled to the next esterification reaction to utilize the solvent therein and to recover the ester product, or, alternatively, the recovery composition can be simply treated, for example by vacuum distillation, to recover the ester product therefrom. When recycling the recovery composition to the next reaction, it is preferred that the same alcohol be used to re-slurry the filter cake as is to be used in the esterification reaction. Returning the stream to the reaction step has been found to have no ill effects to the quality of subsequent products and eliminates the need for vacuum distillation of the recovery composition. Selection of the same alcohol is not only important to ensure that subsequent reaction products include consistent alkyl moieties, but, in addition, economy of the method is enhanced because the need for solvent streams and storage tanks is minimized. It is therefore seen that the alcohol can be removed from the recovery composition or the entire recovery composition can be returned to the reaction step.

Products may be made according to the invention that have purities of at least about 96%, and Gardner colors of no greater than about 1 Gardner unit. Inventive methods also feature excellent yield of at least about 95% and ester products have extremely low acidity, i.e., less than about 0.05 meq/100 g. Additionally, residual titanium contamination in the ester product is typically less than about 0.1 ppm. It has also been found that, where high assay tetrahalophthalic compounds are used as starting materials, the tetrahalophthalate ester produced in accordance with the invention has an assay of about 97%.

While the invention has been described in detail in the foregoing description, the same is to be considered as illustrative and not restrictive in character, it being understood that only the preferred embodiments have been described and that all changes and modifications that come within the spirit of the invention are desired to be protected. The invention will be further described with reference to the following specific Examples. It will be understood that these Examples are also illustrative and not restrictive in nature.

EXAMPLE ONE

Tetrabromophthalic anhydride (463 g) and 2-ethylhexanol (390 g) were charged to a 1000 mL 3-neck round bottom flask equipped with mechanical stirrer, heating mantle with thermocouple and temperature controller, Dean-Stark trap, and reflux condenser. Sodium carbonate was then added to the reaction vessel. The charge of sodium carbonate was calculated by the following equation:

$$gNa_2CO_3 = \frac{g\,PHT\text{-}4 \times (\%H_2SO_4 - 0.02)}{1} \times \frac{106.1}{100 \times 98.08}$$

Example for 1391.1 g of PHT-4 with 0.14% $H_2SO_4$ g $Na_2CO_3$ = 1391.1 × (0.14 − 0.02) × 0.010818 = 1.81 g where the $\%H_2SO_4$ is the residual sulfuric acid in the tetrabromophthalic anhydride. The reaction was stirred for 10 min. to allow for neutralization of PHT-4 and $Ti(OiPr)_4$ (1.8 g) added. The contents were heated to reflux for 8–24 hours. The reaction was complete when the acid number fell below 1 meq/100 g. Solvent was removed from the crude product by vacuum distillation.

Water (7 g) and sodium carbonate (7 g) were added to the stripped product and stirred for 90° C. After 30 min., the water was removed under reduced pressure. The temperature was increased to 105° C., and activated carbon (7 g), magnesium sulfate (7 g) and filter aid (7 g) was added to the mixture. The slurry was stirred at temperature for 1 hour. The slurry was filtered to produce di-2-ethylhexylphthalate with the following characteristics:

| | |
|---|---|
| Acidity meq/100 g | 0.03 |
| Bromine % | 45 |
| 2-EHA A % GC | 0.09 |
| Gardner Color | 0.7 |
| ICP | |
| Na ppm | ND |
| Mg ppm | ND |
| Ti ppm | ND |
| Turbidity, NTU | 0.7 |
| Yield % | 85 |

EXAMPLE TWO

Activated Carbon Cake Recovery Process

Activated carbon cake (100 g) was slurried with 2-EHA (100 g) and heated to 20–100° C. The slurry was stirred until all clumps were gone and a uniform slurry was formed (about 20 min.). The slurry was then filtered through a bed of diatomaceous earth. The filter cake was then washed with 50–200 g of 2-ethylhexanol.

EXAMPLE THREE

Use Of Recovery Stream

Tetrabromophthalic anhydride (416.7 g), 2-ethylhexanol (197 g) and the filtrate from Example 2 were charged to a 1000 mL 3-neck round bottom flask equipped with mechanical stirrer, heating mantle with thermocouple and temperature controller, Dean-Stark trap, and reflux condenser. Sodium carbonate was then added to the reaction vessel. The charge of sodium carbonate was calculated by the equation shown in Example 1. The reaction was stirred for 10 minutes to allow for neutralization of PHT-4 and $Ti(OiPr)_4$ (1.8 g) was added. The contents were heated to reflux for 8–24 hours. The reactions were complete when the acid number fell below 1 meq/100 g. Solvent was removed from the crude product by vacuum distillation.

Water (7 g) and sodium carbonate (7 g) was added to the stripped product and stirred at about 90° C. After 30 min., the water was removed under reduced pressure. The temperature was increased to 105° C., and activated carbon (7 g), magnesium sulfate (7 g) and filter aid (7 g) was added to the mixture. The slurry was stirred at temperature for 1 hour. The slurry was filtered to produce di-(2-ethylhexyl) tetrabromophthalate with the following characteristics.

| | |
|---|---|
| Acidity meq/100 g | 0.01 |
| Bromine % | 44.8 |
| 2-EHA A % GC | 0.09 |
| Gardner Color | 0.9 |
| ICP | |
| Na ppm | ND |
| Ti ppm | ND |
| Mg ppm | ND |
| Turbidity, NTU | 2 |
| Yield % | 93.2 |

EXAMPLE FOUR

Comparative Example

Tetrabromophthalic anhydride (463 g) and 2-ethylhexanol (390 g) were charged to a 1000 mL 3-neck round bottom flask equipped with mechanical stirrer, heating mantle with thermocouple and temperature controller, Dean-Stark trap, and reflux condenser. Magnesium acetate tetrahydrate (1.54 g) was then added to the reaction vessel. The reaction was stirred at 130° C. for 30 min. to allow for neutralization of PHT-4 and $Ti(OiPr)_4$ (1.8 g) was added. The contents were heated to reflux until the acid number was 0.8 meq/100 g. Solvent was removed from the crude product by steam distillation.

Water (7 g) and magnesol (7 g) were added to the stripped product and stirred for 3 hours at 90° C. The slurry was filtered to produce di-2-ethylhexylphthalate with the following characteristics.

| | |
|---|---|
| Acidity meq/100 g | 0.07 |
| Bromine % | 45 |
| 2-EHA A % GC | 0.5 |
| Gardner Color | 4.7 |
| ICP Na ppm | 3.7 |
| ICP Ti ppm | 4.3 |
| ICP Mg ppm | 5.6 |
| Turbidity, NTU | 3 |

EXAMPLE FIVE

Comparative Example

2-Ethylhexanol (1172.1 g) PHT-4 (1391.1 g) and sodium carbonate were charged to the reaction flask and agitation was begun. The charge was stirred for 10 min. to allow for neutralization of PHT-4. The sodium carbonate charge was calculated by the following equation.

$$g\,Na_2CO_3 = \frac{g\,PHT\text{-}4 \times (\%\,H_2SO_4 - 0.02)}{1} \times \frac{106.1}{100 \times 98.08}$$

Example for 1391.1 g of PHT-4 with 0.14% $H_2SO_4$ $g\,Na_2CO_3 = 1391.1 \times (0.14 - 0.02) \times 0.010818 = 1.81\,g$ $Ti(OiPr)_4$ (5.7 g) was added and the contents were heated to reflux and held for 8–12 hours. Reaction was complete when the acid number fell below 3 meq/100 g. Heat was removed and the reaction was cooled to 60° C.

To the reaction mixture was added water (300 g) and oxalic acid dihydrate (12 g). The mixture was stirred for 15 min. at 60° C. The mixture was transferred to a separatory funnel and allowed to separate for 15 min. The product layer was returned to the flask. The product phase was washed with water (300 g) for 15 min at 60° C. The mixture was transferred to a separatory funnel and allow to separate for 15 min. The product layer was returned to the flask and water (300 g) and soda ash (3 g) was added. The mixture was stirred for 15 min. at 60° C. then transferred to a separatory funnel and allowed to separate for 15 min. The product layer was returned to the flask and washed with water for 15 min. at 60° C. The mixture was transferred to a separatory funnel and allowed to separate for 15 min. The product layer was stripped on a wiped film evaporator with the jacket temperature at 150° C. and a vacuum of <2-mm Hg.

| Typical analysis results | |
|---|---|
| Acidity meq/100 g | 0.03 |
| Bromine % | 44 |
| 2-EHA A % GC | 0.24 |
| Gardner Color | 3 |
| ICP Na ppm | 181 |
| ICP Ti ppm | 2 |
| Turbidity, NTU | 11.1 |

EXAMPLE SIX

Comparison of Heat Stability

Tetrabromodioctylphthalate produced by Example 5 method and as in Example 1 method (preferred process) were heated with stirring at 140° C. and samples taken at regular intervals and acidity and turbidity measured.

| | Prepared as in Example 1 | | Prepared as in Example 5 | |
|---|---|---|---|---|
| Time | Acidity (meq/100 g) | Haze | Acidity (meq/100 g) | Haze |
| 0 | 0.03 | 0.6 | 0.03 | 5.0 |
| 30 min. | 0.03 | 1.2 | 0.036 | 9 |
| 2 hrs. | 0.05 | 1.5 | 0.04 | 24 |
| 4 hrs. 30 min. | 0.2 | 1.4 | 0.3 | 83 |

Turbidity rose rapidly in the Example 5 sample (turbidity caused by decomposition and solid impurities being precipitated) while not in Example 1 material. The final acidity was also lower in the sample made via the preferred process.

EXAMPLE SEVEN

Comparison of Hydrolysis Additives

A stripped product was prepared as in Example 1, except that different amounts of water and/or sodium carbonate were used for hydrolysis of the catalyst. One half of a batch prepared in accordance with Example 1 was hydrolyzed using the recipes shown below, and the resulting nonaqueous intermediate was filtered through the same configuration each time, which was a 600 ml course porosity filter that had 15 g of celatom as the filter bed. The filter was maintained at about 100° C.

| Additive for Hydrolysis | Carbon Breakthrough | Time to Complete Filtration |
|---|---|---|
| None | Yes | 120 min. |
| 3 g water | No | 18.5 min. |
| 6 g water | No | 8.5 min. |
| 18 g water | No | 3.5 min. |
| 3 g water, 0.1 g $Na_2CO_3$ | No | 7.5 min. |
| 3 g water, 0.6 g $Na_2CO_3$ | No | 4.0 min. |
| 3 g water, 3 g $Na_2CO_3$ | No | 4.5 min. |

EXAMPLE EIGHT

Industrial Scale Model

Tetrabromophthalic anhydride (20,000 pounds) and 2-ethylhexanol (17,000 pounds) were charged to a 4,000 gallon glass lined reactor and heated to reflux (typically about 200–210° C.). Sodium carbonate was then added to the reaction vessel. The charge of sodium carbonate was calculated by the following equation:

$$lb.\,Na_2CO_3 = \frac{lb.\,PHT\text{-}4 \times (\%\,H_2SO_4 - 0.02)}{1} \times \frac{106.1}{100 \times 98.08}$$

Example for 20,000 lb of PHT-4 with 0.06% $H_2SO_4$ $lb\,Na_2CO_3 = 20,000 \times (0.06 - 0.02) \times 0.010818 = 8.6\,lb.$ The reaction was stirred for 10 min. to allow for neutralization of PHT-4 and then 90 pounds of Tyzor-tpt $Ti(OiPr)_4$ was added. The contents were heated to reflux with the removal of water via a decanter system for 8–24 hours. The reaction was complete when the acid number fell below 1 meq/100 g. Excess alcohol was removed from the crude product by passing through a wiped film evaporator.

The stripped material was pumped into a 4,000 gallon reactor equipped with agitation and vacuum stripping capabilities. The mixture was cooled to about 90° C. and 42 gallons of water and 300 pounds of sodium carbonate were added. The aqueous intermediate was stirred with heating at 100° C. for one hour. After about one hour, a vacuum was applied and the water was removed.

Activated carbon (200 pounds, Darco KB) and MAGNASOL (200 pounds) were then added to the mixture with stirring. More water was removed by vacuum stripping (water in carbon) and the resulting slurry was filtered through a vacuum drum filter with a pre-coat of Celatom FW20 to yield the final product with the following characteristics:

| | |
|---|---|
| Acidity meq/100 g | <0.05 |
| Bromine % | 45% |
| 2-EHA A % GC | <0.3% |
| Gardner Color | <1 |
| ICP | |
| Na ppm | <0.1 ppm |
| Ti ppm | <0.1 ppm |
| Turbidity, NTU | <2 |

What is claimed is:

1. A method for making a tetrahalophthalate ester featuring reduced levels of metal ion contamination, color body contamination and acidity, comprising:

providing a pretreated mixture including a tetrahalophthalic compound, a first organic alcohol, sulfuric acid and a member selected from the group consisting of sodium carbonate, sodium bicarbonate, potassium carbonate, potassium bicarbonate or a combination thereof; wherein the sulfuric acid:tetrahalophthalic compound ratio is less than about 4:10,000 by weight;

subjecting the pretreated mixture to reflux conditions in the presence of a titanate catalyst for a period of time effective to yield a crude reaction product, the crude reaction product including a tetrahalophthalate ester, a portion of the first organic alcohol that remained unreacted and the titanate catalyst;

removing a substantial portion of the first organic alcohol from the crude reaction product to provide a stripped product;

hydrolyzing the titanate catalyst in the stripped product by introducing an aqueous base selected from the group consisting of sodium carbonate, sodium bicarbonate, potassium carbonate, potassium bicarbonate and a combination thereof into the stripped product to provide an aqueous intermediate;

removing water from the aqueous intermediate to provide a nonaqueous intermediate;

dispersing a solid adsorbent into the nonaqueous intermediate to provide a slurry; and filtering the slurry to produce a filter cake and a tetrahalophthalate ester product.

2. The method according to claim 1, wherein said providing comprises:

providing a mixture including a first organic alcohol and a tetrahalophthalic compound, wherein the mixture further includes sulfuric acid in a sulfuric acid:tetrahalophthalic compound ratio of at least about 4:10,000 by weight;

pretreating the mixture to reduce the acidity of the mixture and provide a pretreated mixture having a sulfuric acid:tetrahalophthalic compound ratio of less than about 4:10,000 by weight, wherein said pretreating comprises introducing into the mixture a substantially dry member selected from the group consisting of sodium carbonate, sodium bicarbonate, potassium carbonate, potassium bicarbonate or a combination thereof in an amount effective to reduce the acidity.

3. The method according to claim 2, wherein said pretreating comprises introducing into the mixture substantially dry sodium carbonate in an amount determined by the following equation:

$$gNa_2CO_3 = \frac{g\,PHT\text{-}4 \times (\%H_2SO_4 - N)}{1} \times \frac{106.1}{100 \times 98.08}$$

wherein "g PHT-4" is the mass in grams of the tetrabromophthalic anhydride; wherein "%$H_2SO_4$" is the weight percent of $H_2SO_4$ as compared to the mass of the tetrabromophthalic compound; wherein "N" is the desired weight percent of $H_2SO_4$ in the pretreated mixture and is from about 0.01 to about 0.04; and wherein "$gNa_2CO_3$" is the mass in grams of sodium carbonate that is introduced into the mixture.

4. The method according to claim 1, wherein said providing comprises:

providing a composition including tetrahalophthalic compound, wherein the composition further includes sulfuric acid in a sulfuric acid:tetrahalophthalic compound ratio of at least about 4:10,000 by weight;

pretreating the composition to provide a pretreated composition having reduced acidity, the composition having a sulfuric acid:tetrahalophthalic compound ratio of less than about 4:10,000 by weight, wherein said pretreating comprises introducing into the composition a substantially dry member selected from the group consisting of sodium carbonate, sodium bicarbonate, potassium carbonate, potassium bicarbonate or a combination thereof in an amount effective to reduce the acidity; and mixing an organic alcohol with the pretreated composition to provide a pretreated mixture.

5. The method according to claim 4, wherein said pretreating comprises introducing into the composition substantially dry sodium carbonate in an amount determined by the following equation:

$$gNa_2CO_3 = \frac{g\,PHT\text{-}4 \times (\%H_2SO_4 - N)}{1} \times \frac{106.1}{100 \times 98.08}$$

wherein "g PHT-4" is the mass in grams of the tetrabromophthalic anhydride; wherein "%$H_2SO_4$" is the weight percent of $H_2SO_4$ as compared to the mass of the tetrabromophthalic compound; wherein "N" is the desired weight percent of $H_2SO_4$ in the pretreated composition and is from about 0.01 to about 0.04; and wherein "$gNa_2CO_3$" is the mass in grams of sodium carbonate that is introduced into the mixture.

6. The method according to claim 1, wherein said providing comprises:

providing a substantially dry composition including tetrahalophthalic compound, wherein the composition further includes sulfuric acid in a sulfuric acid:tetrahalophthalic compound ratio of at least about 4:10,000 by weight;

providing a substantially dry organic alcohol;
providing a substantially dry member selected from the group consisting of sodium carbonate, sodium bicarbonate, potassium carbonate, potassium bicarbonate or a combination thereof;
mixing the composition, the alcohol and the member to provide a pretreated mixture having a sulfuric acid:tetrahalophthalic compound ratio of less than about 4:10,000 by weight.

7. The method according to claim 1, wherein the tetrahalophthalic compound comprises a member selected from the group consisting of a tetrahalophthalic acid and a tetrahalophthalic anhydride.

8. The method according to claim 1 wherein said first organic alcohol removing comprises removing a substantial portion of the first organic alcohol from the crude reaction product by vacuum distillation to provide a stripped product.

9. The method according to claim 1 wherein said water removing comprises removing water from the aqueous intermediate by vacuum distillation to provide a nonaqueous intermediate.

10. The method according to claim 1, wherein the adsorbent comprises a member selected from the group consisting of activated carbon, magnesium silicate, diatomaceous earth and combinations thereof.

11. The method according to claim 1, wherein the adsorbent comprises activated carbon.

12. The method according to claim 1, wherein the first organic alcohol is a primary or secondary alkanol with linear or branched alkyl moieties, the alcohol having from about 1 to about 18 carbon atoms.

13. The method according to claim 12, wherein the alcohol has from about 4 to about 16 carbon atoms.

14. The method according to claim 1, wherein the first organic alcohol is 2-ethylhexanol.

15. The method according to claim 1, wherein the titanate catalyst is an alkyl titanate.

16. The method according to claim 1, wherein the titanate catalyst is selected from the group consisting of 2-ethylhexanol titanate, octyl titanate, isopropyl titanate, butyl titanate and mixtures thereof.

17. The method according to claim 1, wherein, the pretreated mixture comprises from about 0.01 to about 0.04 weight percent sulfuric acid as compared to the mass of the tetrabromophthalic compound.

18. The method according to claim 1, wherein said subjecting comprises maintaining the pretreated mixture at a temperature of from about 180° C. to about 260° C.

19. The method according to claim 1, wherein the reflux conditions include a reflux environment and wherein said subjecting further comprises removing water from the reflux environment as a reaction byproduct.

20. The method according to claim 1, wherein said subjecting comprises maintaining the pretreated mixture at a temperature of from about 190° C. to about 220° C.

21. The method according to claim 1, wherein said subjecting comprises subjecting the pretreated mixture to reflux conditions in the presence of a titanate catalyst for a time period of from about 3 hours to about 24 hours.

22. The method according to claim 1, wherein said subjecting comprises subjecting the pretreated mixture to reflux conditions in the presence of a titanate catalyst for a time period ending when the acid value in the crude reaction product is less than about 1 meq/100 g.

23. The method according to claim 22, wherein the acid value is measured by titrating the crude reaction product against bromothymol blue.

24. The method according to claim 1, wherein said hydrolyzing comprises introducing an aqueous base selected from the group consisting of sodium carbonate, sodium bicarbonate, potassium carbonate, potassium bicarbonate and a combination thereof into the stripped product and stirring the aqueous intermediate at a temperature of from about 20° C. to about 100° C. for a time period of from about 1 to about 4 hours.

25. The method according to claim 24, wherein the aqueous base is sodium carbonate.

26. The method according to claim 24, wherein the ratio of sodium carbonate:stripped product in the aqueous intermediate is from about 0.1:100 to about 5:100.

27. The method according to claim 24, wherein the ratio of sodium carbonate:stripped product in the aqueous intermediate is about 1:100.

28. The method according to claim 1, wherein the ratio of water:stripped product in the aqueous intermediate is from about 0.1:100 to about 5:100.

29. The method according to claim 1, wherein the ratio of water:stripped product in the aqueous intermediate is about 1:100.

30. The method according to claim 1, wherein said dispersing comprises stirring the slurry for at least about 30 minutes at a temperature of from about 60° C. to about 150° C.

31. The method according to claim 1, wherein said dispersing comprises stirring the slurry for at least 30 minutes at a temperature of from about 90° C. to about 115° C.

32. The method according to claim 1, wherein said dispersing comprises stirring the slurry for a time period of from about 1 hour to about 24 hours at a temperature of from about 60° C. to about 150° C.

33. The method according to claim 1, wherein said filtering comprises passing the slurry through a bed of diatomaceous earth.

34. The method according to claim 1, wherein the filter cake includes a portion of unrecovered tetrahalophthalate ester, and wherein said method further comprises:
dispersing the filter cake in a solvent to provide a second slurry; and
filtering the second slurry to provide a recovery composition comprising the solvent and a recovered tetrahalophthalate ester product.

35. The method according to claim 34, wherein the solvent comprises a second organic alcohol that is substantially the same composition as the first organic alcohol.

36. The method according to claim 34, wherein the solvent comprises a second organic alcohol.

37. The method according to claim 34, further comprising:
combining the recovery composition with a second quantity of a tetrahalophthalic compound; and
reacting the tetrahalophthalic compound with the second organic alcohol to produce a second tetrahalophthalate ester product.

38. The method according to claim 34, further comprising removing the solvent from the recovery composition to provide a third tetrabromophthalate ester product.

* * * * *